(12) United States Patent
Scholler et al.

(10) Patent No.: US 12,733,792 B2
(45) Date of Patent: Sep. 15, 2026

(54) MINIMALLY INVASIVE OPTICAL FORWARD VIEWING PROBE

(71) Applicant: Clee Medical SA, Geneva (CH)

(72) Inventors: Jules René Raymond Scholler, Saint-Cergues (FR); Gary Evans, Allinges (FR); Michalina Gora-Gioux, St-Prex (CH); Yoseline Cabara, Geneva (CH); Simon Thiele, Stuttgart (DE); Matthew Lapinski, Geneva (CH)

(73) Assignee: CLEE MEDICAL SA, Geneva (CH)

( * ) Notice: Subject to any disclaimer, the term of this patent is extended or adjusted under 35 U.S.C. 154(b) by 210 days.

(21) Appl. No.: 18/525,328

(22) Filed: Nov. 30, 2023

(65) Prior Publication Data

US 2025/0176802 A1 Jun. 5, 2025

(51) Int. Cl.

| | |
|---|---|
| ***A61B 1/00*** | (2006.01) |
| ***A61B 1/07*** | (2006.01) |
| ***A61B 5/00*** | (2006.01) |
| ***G02B 6/26*** | (2006.01) |

(52) U.S. Cl.

CPC ...... *A61B 1/00096* (2013.01); *A61B 1/00126* (2013.01); *A61B 1/0016* (2013.01); *A61B 1/07* (2013.01); *A61B 5/0066* (2013.01); *G02B 6/262* (2013.01)

(58) Field of Classification Search

CPC .............. G01B 9/0205; A61B 1/00096; A61B 1/00172; G02B 6/3624

See application file for complete search history.

(56) References Cited

U.S. PATENT DOCUMENTS

| | | | |
|---|---|---|---|
| 6,134,003 | A | 10/2000 | Tearney et al. |
| 6,564,087 | B1 | 5/2003 | Pitris et al. |
| 7,261,687 | B2 | 8/2007 | Yang |
| 8,789,983 | B2 | 7/2014 | Parkyn |
| 9,131,848 | B2 | 9/2015 | Sinclair |
| 9,474,447 | B2 | 10/2016 | Schmidtlin et al. |

(Continued)

FOREIGN PATENT DOCUMENTS

| | | |
|---|---|---|
| EP | 0883793 A1 | 12/1998 |
| EP | 1512939 A1 | 3/2005 |

(Continued)

OTHER PUBLICATIONS

International Search Report and Written Opinion received for PCT Patent Application No. PCT/IB2023/062100, mailed on Jun. 21, 2024, 14 pages.

(Continued)

*Primary Examiner* — Eric Wong
(74) *Attorney, Agent, or Firm* — HAMILTON, BROOK, SMITH & REYNOLDS, P.C.

(57) ABSTRACT

An optical probe assembly including a lens assembly extending along a central axis for optically coupling to an optical fiber. The lens assembly can have a forward facing exit window. The exit window can have an exit lens with a convex exit surface. The exit lens can extend from a periphery of the exit window and terminate partway across the exit window. The convex exit surface of the exit lens can be tilted inwardly relative to the central axis. The exit lens can bend light received from the optical fiber forwardly out of the exit window at an outward angle relative to the central axis.

42 Claims, 8 Drawing Sheets

(56) References Cited

U.S. PATENT DOCUMENTS 9,574,870 B2 2/2017 Yamazaki et al.
9,658,439 B2 5/2017 Zhu et al.
9,709,749 B2 7/2017 Yamazaki et al.
9,869,821 B2 1/2018 Yamazaki et al.
9,968,245 B2 5/2018 Tearney et al.
10,422,621 B2 9/2019 Yamazaki et al.
10,646,111 B2 5/2020 Wang
11,013,402 B2 5/2021 Li et al.
11,234,751 B2 2/2022 Rollins et al.
11,304,596 B2 4/2022 Gora et al.
11,421,976 B2 8/2022 Hariyama et al.
2005/0234345 A1* 10/2005 Yang .................. A61B 1/00096 600/476
2006/0165350 A1 7/2006 Gelikonov et al.
2008/0304074 A1 12/2008 Brennan, III
2011/0316029 A1 12/2011 Maruyama et al.
2012/0243251 A1 9/2012 Suzuki et al.
2013/0267776 A1 10/2013 Brennan et al.
2013/0310643 A1 11/2013 Gora et al.
2014/0276108 A1 9/2014 Vertikov
2015/0094993 A1 4/2015 Zhu et al.
2015/0116842 A1 4/2015 Zhu et al.
2015/0164311 A1* 6/2015 Yu .......................... A61B 3/102 600/478
2015/0351629 A1* 12/2015 Wheatley ........... G01B 9/02059 600/425
2016/0018581 A1 1/2016 Maruyama et al.
2016/0153765 A1 6/2016 Yamazaki et al.
2016/0341545 A1 11/2016 Yamazaki et al.
2018/0087893 A1 3/2018 Sasaki et al.
2020/0139092 A1 5/2020 Tearney et al.
2021/0173061 A1 6/2021 Fyler et al.
2021/0267442 A1 9/2021 Petersen et al.
2023/0320576 A1 10/2023 Feldman et al.
2023/0333360 A1 10/2023 Hillman et al.
2025/0116816 A1* 4/2025 Marple ................. G01J 3/0218

FOREIGN PATENT DOCUMENTS

EP 2160217 A1 3/2010
EP 1750569 B1 5/2012
EP 2515150 A1 10/2012
EP 2713847 A2 4/2014
EP 2412298 B1 11/2014
EP 2852315 A1 4/2015
EP 2967279 A2 1/2016
EP 3100669 A1 12/2016
EP 2963467 B1 2/2017
EP 3031381 B1 11/2017
EP 3284387 A1 2/2018
EP 3125742 B1 8/2018
EP 3615121 A1 3/2020
EP 3029415 B1 7/2020
EP 3689220 A2 8/2020
EP 3691512 A1 8/2020
EP 3841736 A1 6/2021
WO 97/32182 A1 9/1997
WO 2000/042906 A2 7/2000
WO 2003/104744 A1 12/2003
WO 2005/094449 A2 10/2005
WO 2008/049118 A2 4/2008
WO 2008/081653 A1 7/2008
WO 2008/154460 A1 12/2008
WO 2010/104752 A2 9/2010
WO 2011/074051 A1 6/2011
WO 2011/108087 A1 9/2011
WO 2012/029685 A1 3/2012
WO 2012/098999 A1 7/2012
WO 2012/147379 A1 11/2012
WO 2012/162493 A2 11/2012
WO 2013/148360 A1 10/2013
WO 2013/177154 A1 11/2013
WO 2014/022649 A2 2/2014
WO 2014/115360 A1 7/2014
WO 2014/115361 A1 7/2014
WO 2014/152474 A2 9/2014
WO 2014/153379 A1 9/2014
WO 2014/155584 A1 10/2014
WO 2014/186121 A2 11/2014
WO 2015/022760 A1 2/2015
WO 2015/025932 A1 2/2015
WO 2015/102081 A1 7/2015
WO 2015/187325 A1 12/2015
WO 2016/167204 A1 10/2016
WO 2016/210132 A1 12/2016
WO 2017/006848 A1 1/2017
WO 2017/037507 A1 3/2017
WO 2017/205373 A1 11/2017
WO 2018/057924 A1 3/2018
WO 2018/200440 A1 11/2018
WO 2019/070782 A1 4/2019
WO 2020/061001 A1 3/2020
WO 2020/072470 A1 4/2020
WO 2020/262262 A1 12/2020

OTHER PUBLICATIONS

Jiawen Li, 3D-Printed Micro Lens-in-Lens for In Vivo Multimodal Microendoscopy, Jan. 1, 2022, Advanced Science News, 1-8.

Jiawen Li, Ultrathin Monolithic 3D printed optical coherence tomography endoscopy for preclinical and clinical use, Sep. 1, 2020, www.nature.com/lsa, 1-10, 9/124, https://dpi.org/10.1038/s41377-020-00365-w.

* cited by examiner

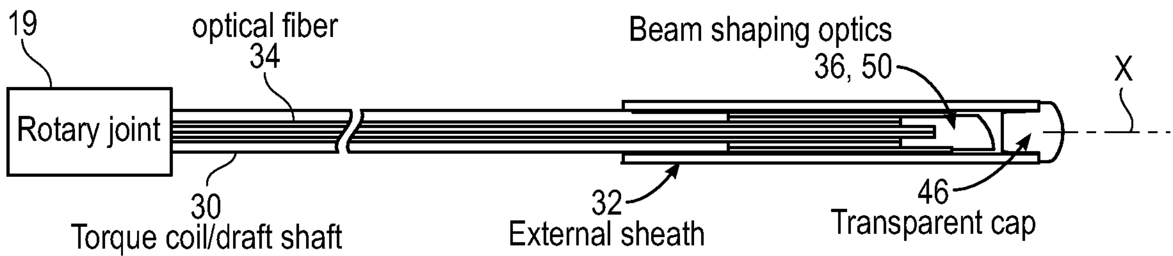
FIG. 1
FIG. 2A
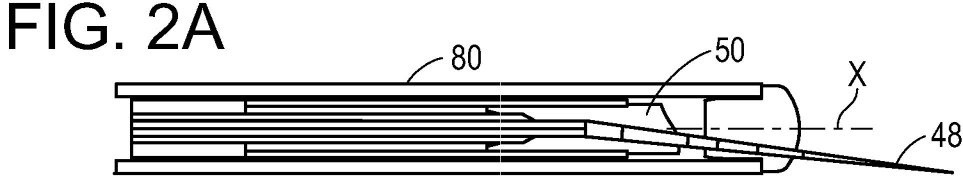
FIG. 2B
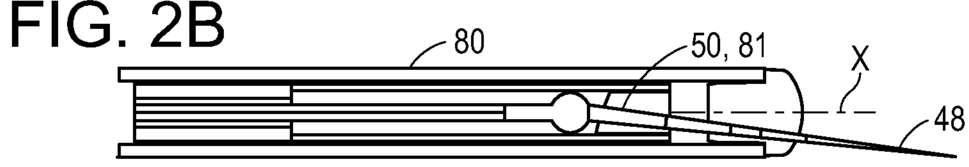
FIG. 2C
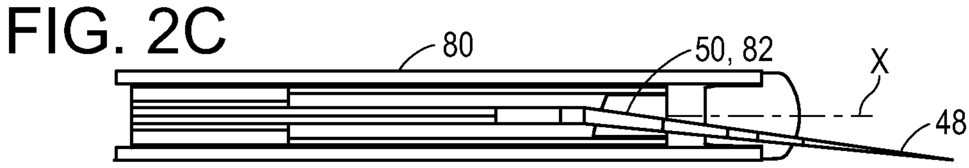
FIG. 2D
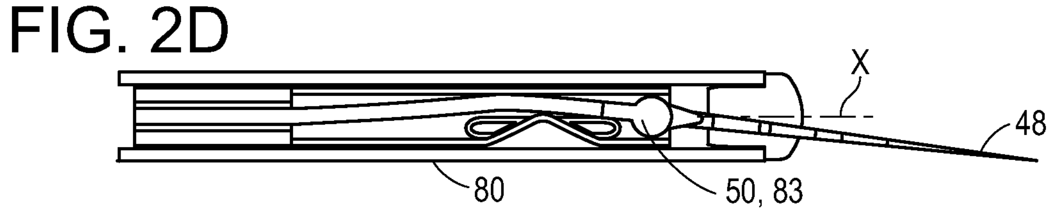

MINIMALLY INVASIVE OPTICAL FORWARD VIEWING PROBE

BACKGROUND

Optical coherence tomography (OCT) is an imaging technique that uses light to probe and acquire the structure of objects of interest with micrometer resolution. The contrast provided by OCT is based on the local variations of the imaged sample refractive index that leads to light being backscattered and detected by the imaging device. The interferometric nature of the measurement yields two important properties: a very high sensitivity and optical sectioning. The first allows to image structures of weakly varying optical refractive index and the latter to acquire such structures in 3D in a non-invasive and non-destructive manner in turbid objects. Owing to these properties, optical coherence tomography is an established biomedical imaging technique that is widely and routinely used, especially in ophthalmology and cardiology.

There are numerous practical implementations of OCT that can use different types of low coherence light source (e.g., superluminescent diodes, broad band lasers, swept source lasers). The light can be guided by means of lenses and propagate in free space—typically for ophthalmology—or guided by means of optical fibers—typically for cardiology.

The scattering properties of biological tissues typically allows one to image a few millimeters deep inside tissues using OCT and therefore limits the clinical application to shallow structures (e.g., skin, retina, arteries wall). Endoscopic OCT probes allow to access deeper structures and can be divided into two categories based on their field of view: side imaging and forward imaging.

Side-imaging probes are more commonly used owing to their easier implementation where the scanning is done on the proximal end of the probe by rotating it to create a disk-shaped B-Scan. To acquire a 3D image of the tissue, the probe is usually pulled-back at a constant speed, creating a helicoidal scanning inside the tissue. Because the actuation is done on the proximal side, side-imaging probes tend to have a small diameter and hence to be flexible. However, such probes only provide side imaging and therefore limit its clinical applications, such as image-based detection of fragile tissue and surgical guidance.

Forward-imaging probes are more suitable for fragile tissue detection and surgical guidance, however forward-imaging probes are more complex to implement and typically requires the actuation to be within or close to the probe tip, leading to larger diameters, rigid distal end and higher prices which are not compatible with single use medical device.

SUMMARY

The present disclosure provides an optical probe assembly including a lens assembly extending along a central axis for optically coupling to an optical fiber. The lens assembly can have a forward facing exit window. The exit window can have an exit lens with a convex exit surface. The exit lens can extend from a periphery of the exit window and terminate partway across the exit window. The convex exit surface of the exit lens can be tilted inwardly relative to the central axis. The exit lens can bend light received from the optical fiber forwardly out of the exit window at an outward angle relative to the central axis.

In particular embodiments, the exit lens can bend and focus the light out of the exit window at an outward angle relative to the central axis. The optical fiber can be included in the optical probe assembly and can be optically coupled to the lens assembly along the central axis for receiving light from a light source. The lens assembly can further include a connecting portion that is integrally formed together with the exit window. The connecting portion can be configured to mechanically couple the lens assembly to the optical fiber. The connecting portion can include a connecting recess extending along the central axis that is configured to receive a distal end of the optical fiber. An inner cannula can house the lens assembly and can be rotationally disposed within an outer cannula. The outer cannula can have a distal end with a transparent cap secured thereto, through which light from the exit window can pass. A telescopic mechanism can be configured to translate the inner cannula and the lens assembly relative to the outer cannula. The lens assembly can include a mechanical stop that is configured to limit a telescoping depth of the inner cannula relative to the outer cannula. A rotational element can be disposed at a proximal end of the optical fiber for rotating a distal end of the optical fiber and the lens assembly. The rotational element can be rotationally coupled to a torque transfer element. A connector assembly can be disposed at the proximal end of the optical fiber for connecting to the light source. The rotational element can be a rotational motor or a rotary joint in operative arrangement with a rotational motor. The lens assembly can include a reflective surface at a distal end of the connecting recess of the connecting portion that is configured to generate a common path reference light signal. The lens assembly can include an angled surface spaced apart from the distal end of the connecting recess of the connecting portion along the central axis for bending light received from the optical fiber forwardly towards the exit lens at an outward angle relative to the central axis. The angled surface can be at a distal end of an air gap. The exit lens can be a freeform lens in which the convex exit surface can be defined by a high order polynomial. The outer diameter of the lens assembly can range from about 125 to 1200 um. The optical probe assembly can be included in an Optical Coherence Tomography (OCT) system.

The present disclosure can also provide an optical probe assembly including a lens assembly extending along a central axis for optically coupling to an optical fiber. The lens assembly can include a connecting portion that is integrally formed together with a forward facing exit window. The connecting portion can include a connecting recess extending along the central axis for receiving a distal end of the optical fiber. The exit window can have an exit lens. The lens assembly can include an angled surface spaced apart from a distal end of the connecting recess of the connecting portion along the central axis for bending light received from the optical fiber forwardly towards the exit lens at an outward angle relative to the central axis. The exit lens can further bend light received from the angled surface forwardly out of the exit window at a further outward angle relative to the central axis.

In particular embodiments, the angled surface can be at a distal end of an air gap.

The present disclosure can also provide a method of operating an optical probe assembly. The optical probe assembly can include a lens assembly extending along a central axis for optically coupling to an optical fiber. The lens assembly can have a forward facing exit window. The exit window can have an exit lens with a convex exit surface. The exit lens can extend from a periphery of the exit window and terminate partway across the exit window. The convex exit surface of the exit lens can be tilted inwardly relative to the central axis. The method can include conveying light from the optical fiber to the exit lens and bending the light with the exit lens out of the exit window at an outward angle relative to the central axis. The exit lens can be rotated about the central axis and direct the light forwardly in an expanding conical pattern for creating images forward of the probe assembly.

In particular embodiments, the exit lens can bend and focus the light out of the exit window at an outward angle relative to the central axis. Light can be delivered from the light source to the optical fiber. The lens assembly can further include a connecting portion that is integrally formed with the exit window. The connecting portion can be configured to mechanically couple the lens assembly to the optical fiber. The connection portion can have a connecting recess extending along the central axis that is configured to receive a distal end of the optical fiber. An inner cannular can house the lens assembly and can be rotationally disposed within an outer cannula. The outer cannula can have a distal end with a transparent cap secured thereto, through which light from the exit window can pass. The inner cannula and lens assembly can be translated relative to the outer cannula with a telescopic mechanism. Telescoping depth of the inner cannula relative to the outer cannula can be limited with a mechanical stop included with the lens assembly. A distal end of the optical fiber and the lens assembly can be rotated with a rotational element disposed at a proximal end of the optical fiber. The rotational element can be rotationally coupled to a torque transfer element. A connector assembly can be disposed at the proximal end of the optical fiber for connecting to the light source. Rotation can be provided with the rotational element, which can be a rotational motor or a rotary joint in operative arrangement with a rotational motor. A common path reference light signal can be generated with a reflective surface at a distal end of the connecting recess of the connecting portion of the lens assembly. Light received from the optical fiber can be bent forwardly towards the exit lens at an outward angle relative to the central axis with an angled surface spaced apart from the distal end of the connecting recess of the connecting portion of the lens assembly along the central axis. The angled surface can be at a distal end of an air gap. In one embodiment, the exit lens can be a freeform lens in which the convex exit surface is defined by a high order polynomial. The outer diameter of the lens assembly can range from about 125 to 1200 μm. The optical probe assembly can be included in an optical coherence tomography system.

The present disclosure can also provide a method of operating an optical probe assembly. The optical probe assembly can include a lens assembly extending along a central axis for optically coupling to an optical fiber. The lens assembly can include a connecting portion that is integrally formed together with a forward facing exit window. The connecting portion can include a connecting recess extending along the central axis for receiving a distal end of the optical fiber. The exit window can have an exit lens. The lens assembly can include an angled surface spaced apart from a distal end of the connecting recess of the connecting portion along the central axis. The method can include using the angled surface to bend light received from the optical fiber forwardly towards the exit lens at an outward angle relative to the central axis. The exit lens further bends light received from the angled surface forwardly out of the exit window at a further outward angle relative to the central axis. The exit lens can be rotated about the central axis and direct the light forwardly in an expanding conical pattern for creating images forward of the probe assembly.

In particular embodiments, the angled surface can be at a distal end of an air gap.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1 is a schematic drawing of an embodiment of an optical probe assembly in the present disclosure.

FIGS. 2A-2D are schematic drawings of different embodiments of the probe heads.

DETAILED DESCRIPTION

Figure 3:
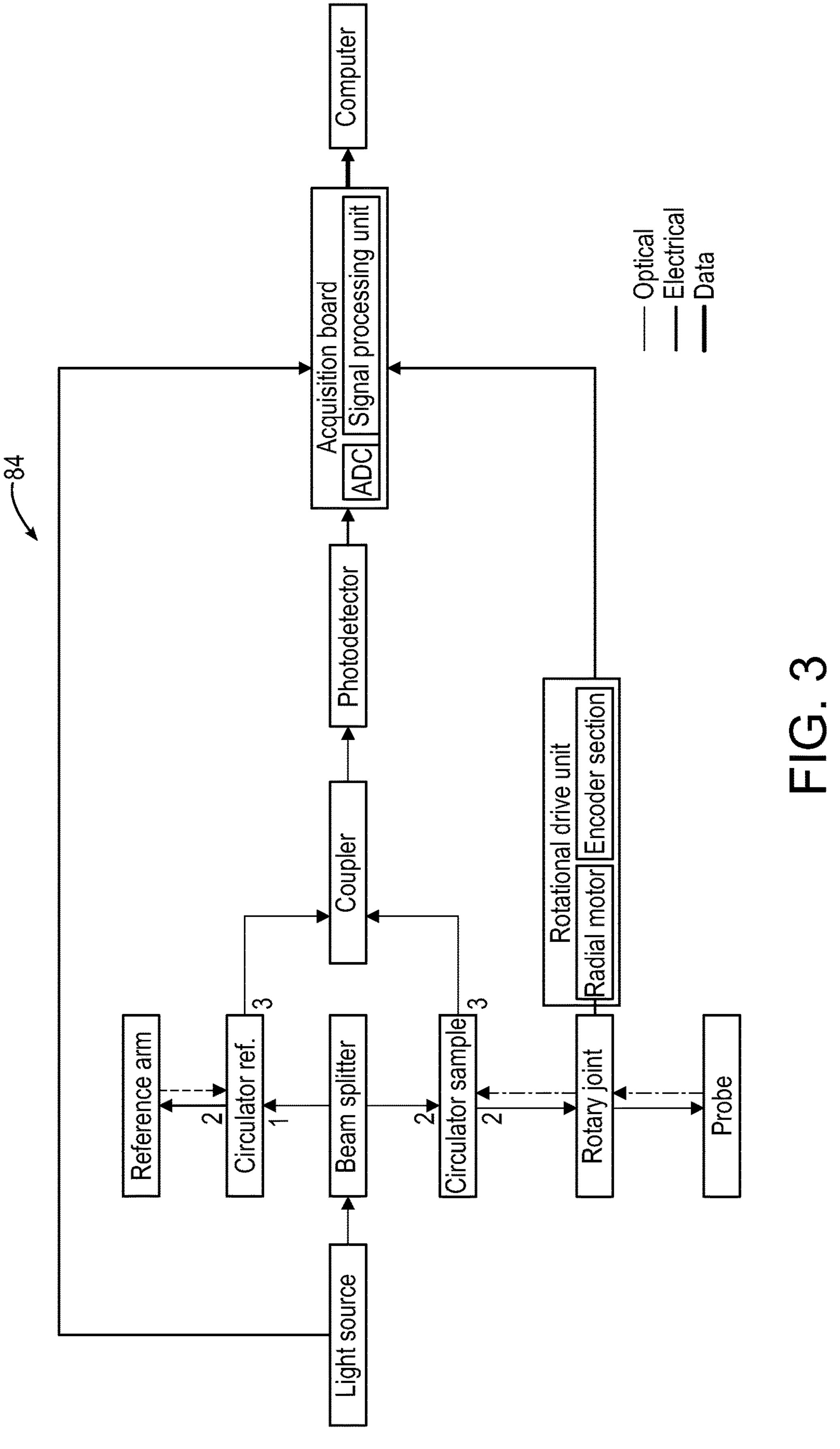
FIG. 3 is a schematic drawing of an OCT set up in a Mach-Zehnder configuration.

A description of example embodiments follows.

FIG. 1 is a schematic drawing of an embodiment of a minimally invasive Optical Coherence Tomography (OCT) forward viewing optical probe or probe assembly 80 for insertion and viewing within structures, including body tissues, structures, lumens or cavities. It can include an optical fiber 34 that guides the light from the proximal to the distal end of the probe 80, a lens 36 or lens-assembly 50 that shapes and guides the light outside of the probe 80 in a controlled manner, a torque coil, inner cannula or a drive shaft 30 that transfers torque applied to the proximal end of the probe 80 to the distal end of the probe 80 and vice-versa, a protective outer cannula, conduit or sheath 32 that allows the drive shaft 30 to rotate freely and be isolated from the outside medium, and a transparent end termination cap, tip or window 46 that encloses the driveshaft 30 in the protective sheath 32.

FIGS. 2A-2D are schematic drawings of embodiments of minimally invasive probe heads with various lens assembly designs. FIG. 2A depicts a freeform (3D printed or 3D etched) lens assembly 50 for bending and focusing light 48. FIG. 2B depicts a lens assembly 50 with a spacer-ball lens—prism 81. FIG. 2C depicts a lens assembly 50 with a spacer-GRIN lens—prism 82. FIG. 2D depicts a lens assembly 50 with a spacer-mechanically tilted ball lens 83.

FIG. 3 is a schematic drawing of an embodiment of an OCT setup 84 in a Mach-Zehnder configuration. The light from a low coherence light source can be split between a reference and a sample path where the object to be imaged is placed. The light can be reflected by the reference arm and recombined with the light backscattered by the imaged object in the sample arm. The light can be recombined by a light coupler and guided to a photodetector that measures the interference signals between the reference and sample light. From the interferometric signal, it is possible to reconstruct the structure of the imaged object.

Figure 4:
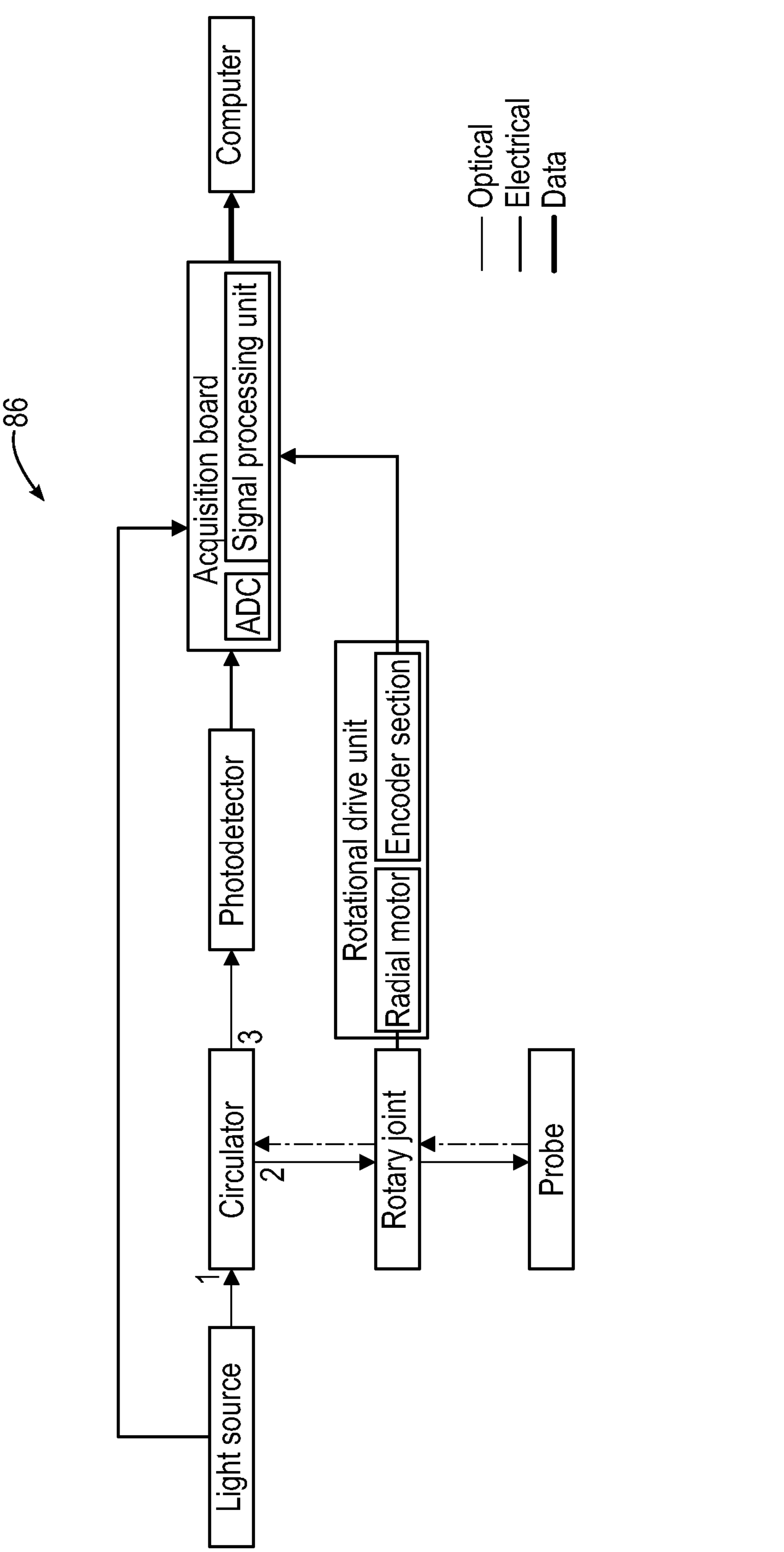
FIG. 4 is a schematic drawing of an embodiment of an OCT setup in a common path configuration.

FIG. 4 is a schematic drawing of an embodiment of an OCT setup 86 in a common path configuration. The light from a low coherence light source can be guided using an optical fiber to the input port of a circulator. The second port of the circulator can be connected to a rotary joint via a separate optical fiber, and the rotary joint can be connected to the embodiment common path probe. The third port of the circulator can be connected to a photodetector via another optical fiber so that any light entering the probe 80 can be guided back to the photodetector.

Optical Probe

The present disclosure provides a minimally invasive Optical Coherence Tomography (OCT) endoscopic forward viewing probe or probe assembly 80 that can image forwardly ahead of the probe, such that any object or structure located on the probe trajectory that can come in contact with the probe can be imaged and detected before contact for example, tissue or body structures within a patient.

Embodiments of the probe or probe assembly 80 can include the following elements (FIG. 1):

i. An optical fiber 34 that guides the light 48 from the proximal to the distal end of the probe 80.
ii. a lens 36 or lens-assembly 50 that shapes and guides the light 48 outside of the probe 80 in a controlled manner.
iii. a drive shaft 30 that transfers torque applied to the proximal end of the probe 80 to the distal end of the probe 80 and vice-versa.
iv. a protective sheath 32 that allows the drive shaft 30 to rotate freely and isolated from the outside medium.
v. a transparent end termination cap, tip or window 46 that encloses the driveshaft 30 in the protective sheath 32.

The probe lens assembly 50 can deviate the light 48 from the direction formed by the probe body (hereafter referred as the central axis X) and collimate the light 48 to create a narrow beam. Without actuating the probe 80, the recorded OCT A-Scan therefore corresponds to a thick line forming an angle with the central axis X.

In an embodiment, an internal surface of the probe can be used as a reference signal for the OCT. This internal surface can be a surface between the fiber 34 and the lens assembly 50, or within the lens assembly 50 or the surface between the lens assembly 50 and the transparent tip 46.

Embodiments of the lens assembly 50 can be implemented in the following manner, but not limited to:

a) A freeform (3D printed or 3D etched) lens assembly 50 (FIG. 2A).
b) A spacer to expand the beam after the optical fiber, a ball lens to collimate/focus the beam and a prism 81 to tilt it from the central axis X (FIG. 2B).
c) A spacer to expand the beam after the optical fiber, a GRIN lens to collimate/focus the beam and a prism 82 to tilt it from the central axis X (FIG. 2C).
d) A spacer to expand the beam after the fiber, a mechanically tilted ball lens 83 to collimate/focus the beam at an angle from the central axis X (FIG. 2D).

OCT Implementation of the Probe

The probe 80 can be connected to the rotating section of an optical rotary joint 19. The optical rotary joint 19 connects a non-rotating section and a rotating section to each other, and allows light transmission between the two sections. The optical rotary joint 19 allows the probe 80 to rotate and to transmit the light from a non-rotating fiber 14 (FIG. 5A), mechanically isolating the rest of the optical system from the probe 80 rotation. In use, the probe 80 can be introduced and advanced into an opening within the patient, while the lens assembly 50 is rotated by the inner cannula 30 inside the outer cannula 32, directing light 48 forwardly out the transparent cap 46 at a rotating angle in an expanding conical pattern or path. The rotating outwardly directed light 48 can be directed onto tissue or body structures forwardly in front of the probe 80 to allow images to be made of structures in front of the advancement of the probe 80. This allows images in front of the probe 80 to be viewed and known prior to advancing the probe 80 forward. If there are structures in front of the probe 80 that might be damaged with advancement of the probe 80, advancement can be stopped.

The rotating section side of the optical rotary joint 19 can be driven to rotate by a radial or rotary motor 18 of a rotational drive unit. The rotational speed and/or the angular position of the radial motor 18 can be detected by an encoder section.

In the two-arm configuration of the interferometer, illustrated here but not limited to a Mach-Zehnder configuration (FIG. 3), the light backscattered by the imaged sample can be guided back by the probe 80 to the optical rotary joint 19 and back to the circulator in the sample arm. The light then exits the circulator on the third port and is recombined by a light coupler which is connected to the photodetector.

In the two-arm configuration of the interferometer, the light coupler can have several implementations, including but not limited to:

a) 2×1 light coupler with single photodetection.
b) 2×2 light coupler with balanced photodetection, where two photodetectors can be used and the differential signal can be measured resulting in the cancellation of common mode noise and increasing the OCT sensitivity.
c) 2×2 polarization maintaining coupler where each output can be connected to a polarization beam splitter and a dual balanced detection can be performed in a polarization diversity measurement scheme.

In the common-path configuration (FIG. 4), the light backscattered by the imaged tissue sample can be guided back by the probe through the optical rotary joint to the second port of the circulator. It then exits the circulator on the third port and can be detected by the photodetector.

The common path configuration (FIG. 4) can allow the use of the biomedical imaging device in a plug and play manner, alleviating the need for matching the reference arm optical path length to each probe (FIG. 1), making it compatible with single use probes of different lengths, and leading to a less complex imaging device that is easier to operate and requires less maintenance than a two-arm equivalent system.

Probe Image Acquisition, Display and Processing

The encoder section can be connected to a data processing unit of an acquisition board enabling, the synchronization of the acquisition of data and therefore the processing and display of data.

The probe rotation created by the rotational drive unit leads the A-Scan line to rotate around the central axis X effectively creating a conical pattern. By recording a plurality of A-Scan lines, a B-Scan can be reconstructed by arranging the plurality of A-Scan lines in a 2D array and gives a cross-sectional view of what is ahead of the probe tip.

The cross-sectional view can be oriented in space and stabilized by using the position signal from the encoder section of the rotational drive unit.

In an alternative implementation, the position of the rotational drive unit can be monitored by measuring the reflection of a laser collimated on the optical rotary joint 19 where a mirror can be secure or glued. Each time the mirror passes on the laser path, a signal can be measured, effectively creating a trigger signal.

The B-Scan can be displayed in real time with each A-Scan being a line in a 2D canvas and for every rotation of the optical rotary joint 19 the encoder section can send a trigger signal to the processing unit so that one image can be displayed and processed per probe rotation.

The probe 80 can be mounted on a guiding device with a linear drive unit composed of a linear translation stage and an encoder section. By displacing the probe 80 forward or backward with the linear drive unit, a plurality of B-Scans can be acquired and arranged to reconstruct a 3D view of the imaged tissue hereafter referred as C-Scans.

To reconstruct the C-Scan in 3D, the angle between the optical beam and the central axis X and the physical position of the probe 80 given by the encoder section of the linear drive unit can be used to translate each B-Scan pixel location into the 3D physical space and obtain an accurate 3D representation of the imaged sample.

The C-Scan or any 2D cross-section of a C-Scan can be reconstructed and displayed in real time when the probe 80 is moved forward or backward.

The C-Scan or C-Scan cross-section real-time reconstruction and display can be done concurrently (at the same time) with the B-Scan real-time display.

The recorded A-scans can be post processed to create angiography and motility contrasts. To this end, a plurality of successive A-Scans, or A-Scans acquired at the same location (e.g., taken at the same angular position between each rotation of the probe 80) can be analyzed together, for e.g., but not limited to, by measuring the speckle decorrelation, by measuring the A-Scans time and/or space fluctuations.

Angiography and motility contrasts A-Scans can be assembled to form B-Scans and C-Scans with angiography and motility contrasts. The different contrast can be overlayed to create multicolored 2D or 3D view of the imaged tissue.

Angiography and motility contrasts B-Scans, C-Scan and C-Scan cross-sections can be reconstructed and displayed in real time.

Referring to FIGS. 5A-5D, in an embodiment of the present disclosure, an Optical Coherence Tomography (OCT) system, device or arrangement 10 can include an Optical Coherence Tomography (OCT) engine, module, cabinet or electronics box 12 that contains a low coherence light source 12*a*. A rotary optical connection 19 receives light from the light source 12*a* and delivers the light to rotating optics or a rotating lens assembly 50 of a disposable forward imaging OCT probe or probe assembly 27.

The light source 12*a* within OCT engine 12 can include superluminescent diodes, broad band lasers, and swept source lasers. Embodiments of the OCT engine 12 can also contain the optics, electronics, controller and acquisition board for operating the OCT system 10. Embodiments can also include the configuration of the interferometer shown in FIG. 3, or the one shown in FIG. 4. An optical conduit or fiberoptic cable 14 can connect the OCT engine 12 to a rotary junction 16 of rotary optical connection 19 for conveying light 48 from the light source 12*a* to the rotary optical connection 19. A motor 18 can be connected or mounted to the rotary junction 16 by a bracket 18*a*. The motor 18 also can be rotatably coupled or connected to the rotary junction 16 by pulley 18*b*, pulley belt 20 and pulley 16*a*. The motor 18 drives the pulley belt 20 to rotate a proximal or first rotary optical connector 40 about a central rotational axis A. The first rotary optical connector 40 can be located within the body 17 of rotary optical connection 19. The proximal rotary optical connector 40 receives light from the stationary fiberoptic cable 14 along optical axis O for converting light from a stationary light conduit to a rotating light conduit.

The disposable OCT probe 27 can be mechanically and optically coupled to the rotary optical connection 19. The OCT probe 27 can have a proximal probe locking connector 22, and a probe head or tip regions 44 connected to the probe locking connector 22 by a rotatable inner torque transfer element, coil, cannula, sheath, tube, drive shaft or conduit 30, and by a stationary protective outer cannula, sheath, tube or conduit 32. The lens assembly 50 can be rotated by the inner cannula 30 within the outer cannula 32.

Figure 7:
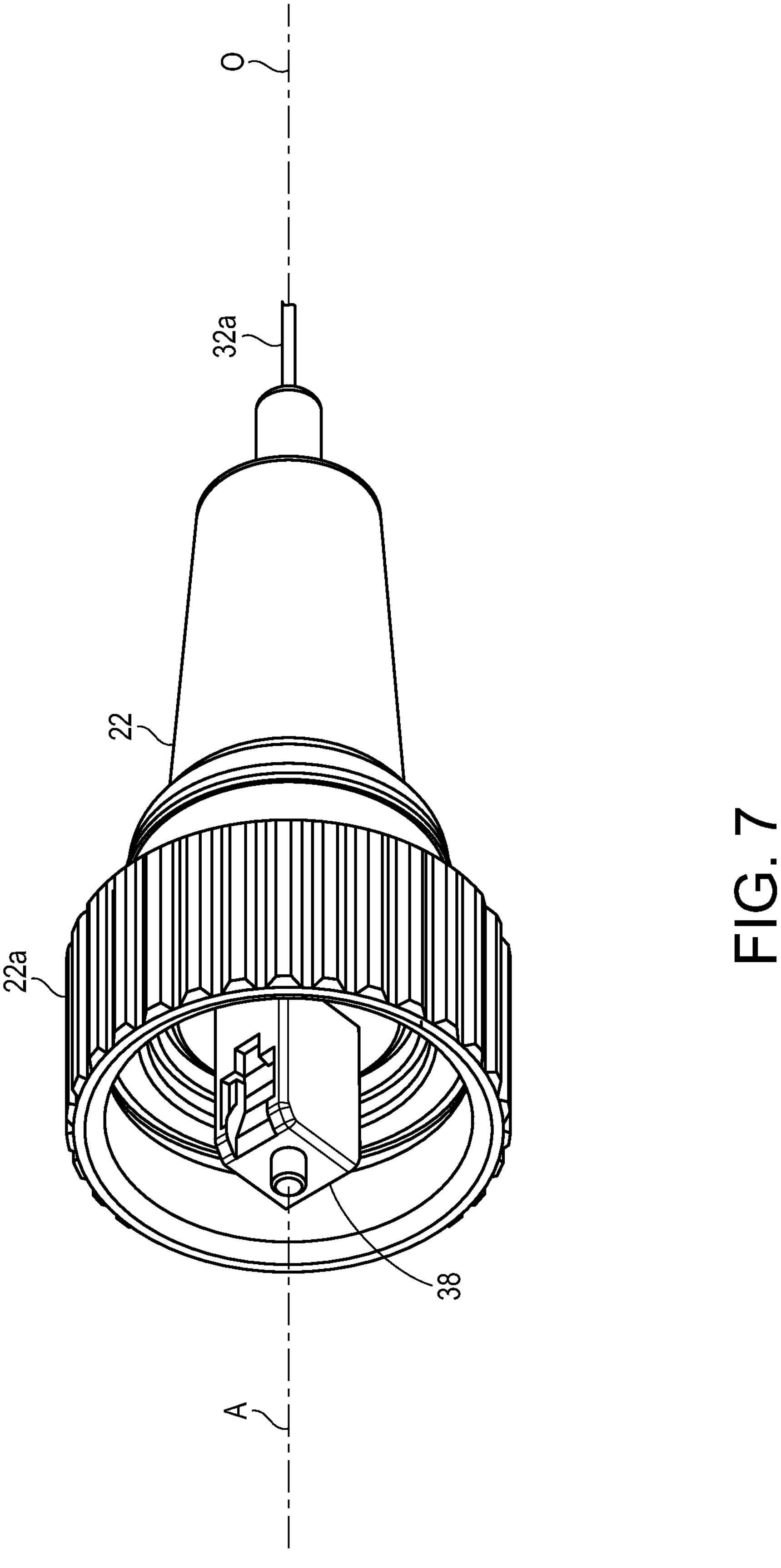
FIG. 7 is a rear perspective view of an embodiment of a probe locking connector of an OCT probe.

The probe locking connector 22 of the OCT probe 27 can be secured to a hub 21 extending from the body 17 of rotary optical connection 19 by a threaded connector locking ring 22*a* that fastens over the outer diameter of hub 21. The rotary or rotatable optical connector 40 can be mechanically and optically connected to a distal or second rotary or rotatable optical connector 38 (FIGS. 5C and 7) located in the probe locking connector 22 of the disposable OCT probe 27 along common axes O and A. The rotatable optical connector 38 extends into the hub 21 to connect with the rotary optical connector 40. The rotatable optical connector 38 can be rotationally coupled and rotationally isolated from the outer stationary locking ring 22*a* and body 22*b* of the probe locking connector 22, so that the rotatable optical connector 38 can rotate within the body 22*b*. A fiber optic or optical fiber 34 can be positioned within the inner cannula 30, and both the proximal ends of the fiber optic 34 and inner cannula 30 can be mounted or secured to the rotatable optical connector 38 along rotational axis A and optical axis O for rotating with the rotatable optical connector 38. The rotatable inner cannula 30 and the fiber optic 34 can extend and rotate about the optical axis O, and the distal ends thereof can be connected, secured or coupled to a lens assembly 50 having a lens or beam shaping optics 36 near or proximate to the probe tip 28. The lens assembly 50 and lens 36 can be rotatable together with the fiber optic 34 and the inner cannula 30.

The inner cannula 30, fiber optic 34 and the lens assembly 50 can be rotatable within the stationary outer cannula 32, which can be formed of more than one section or piece, 32*a*, 32*b* and 32*c*. For example, a first outer stationary cannula piece 32*a* can be secured to the body 22*b* of the probe locking connector 22, and can be slidably connected to a telescopic mechanism, hub, tube, handle or member 24. A second outer stationary cannula piece 32*b* can be secured to the telescopic hub 24, and can be linearly translated for extending or retracting the outer cannula piece 32*b* relative to the inner cannula 30 and fiber optic 34. The length of the second outer cannula piece 32*b* can be extended by a connector hub 26 to which a third outer stationary cannula piece 32*c* can be attached, and the distal end terminating at the probe tip 28. The probe tip 28 can have a distal forward facing outer transparent cap, tip or window 46 mounted or secured to the distal end of the outer cannula piece 32*c* of outer cannula 32. The telescopic hub 24 can slide longitudinally or linearly to translate the outer cannula piece 32*c* of outer cannula 32 relative to the rotating inner cannula 30, the fiber optic 34 and the lens assembly 50, to adjust the spacing between the lens 36 and the transparent cap 46 to optimize optical properties and/or compensate for spacing variations between the lens assembly 50 and the transparent cap 46 caused by bending of the OCT probe 27 during use. In some embodiments, the outer cannula 32 does not need the third outer cannula piece 32*c*.

Figures 5A, 5B, 5C, 5D:
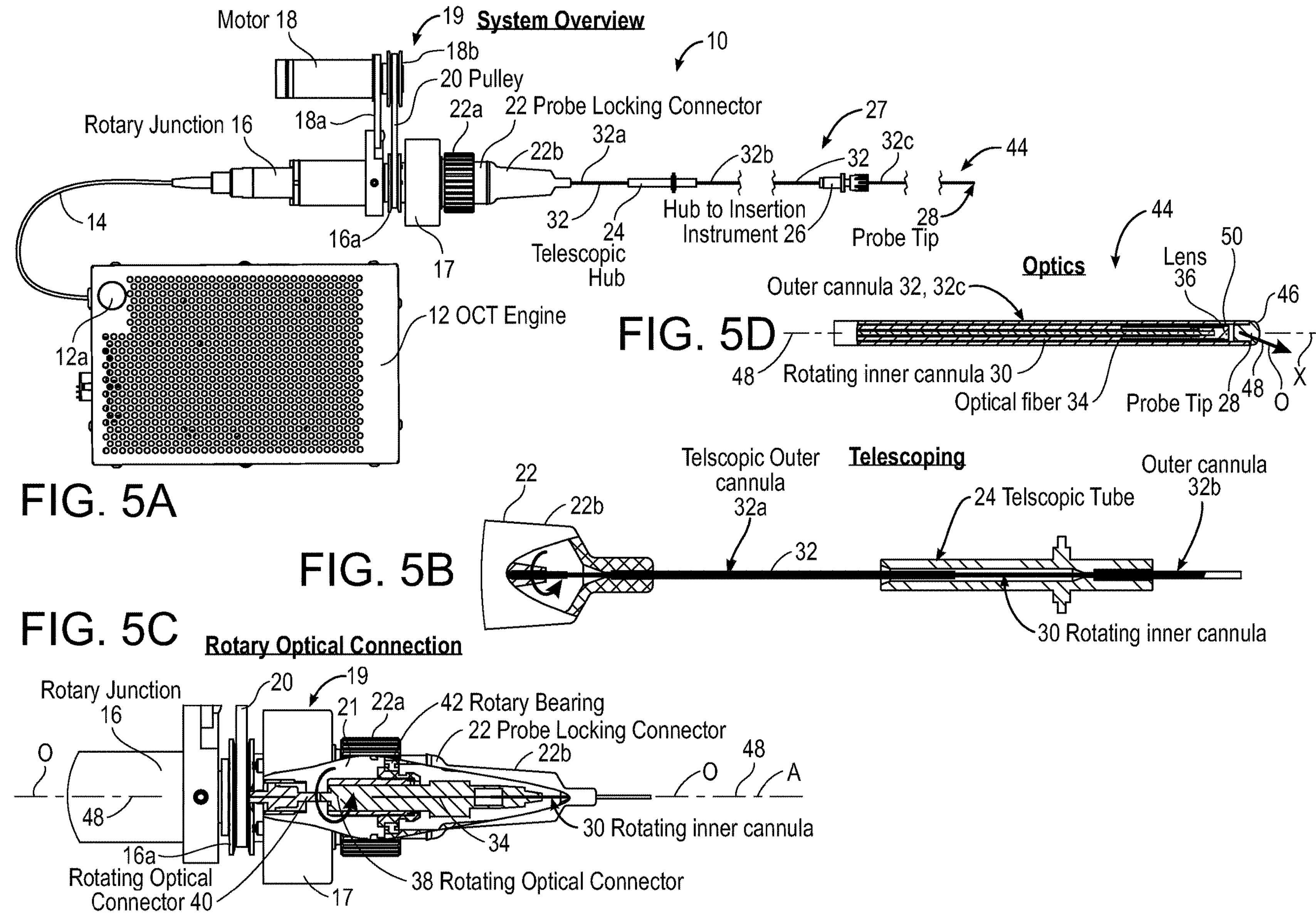
FIGS. 5A-5D depict an embodiment of an OCT system with an embodiment of an optical probe assembly in the present disclosure, with certain features enlarged and in section to show detail.

As seen in FIG. 5D, the probe tip 28 can be at the distal end of the tip region or portion, or probe head 44 of the OCT probe 27. The probe head or tip region 44 can include the stationary outer cannula 32 which can be the third outer cannula piece 32*c*, the rotatable inner cannula 30, rotatable fiber optic 34, the rotatable assembly lens 50 and the stationary transparent cap 46. The outer cannula 32 and transparent cap 46 can provide a fluid tight sealed environment for the inner cannula 30 and lens assembly 50. The fiber optic 34, the inner cannula 30 and lens assembly 50 can rotate about a central longitudinal rotational axis X within the outer cannula 32 at the probe head 44. The lens 36 of the lens assembly 50 can shape, focus and bend the light 48 delivered to the lens 36 by the fiber optic 34 at an angle relative to axis X, and the light 48 can pass out the forward transparent cap 46 forwardly an angle relative to axis X.

Figures 6A, 6B, 6C:
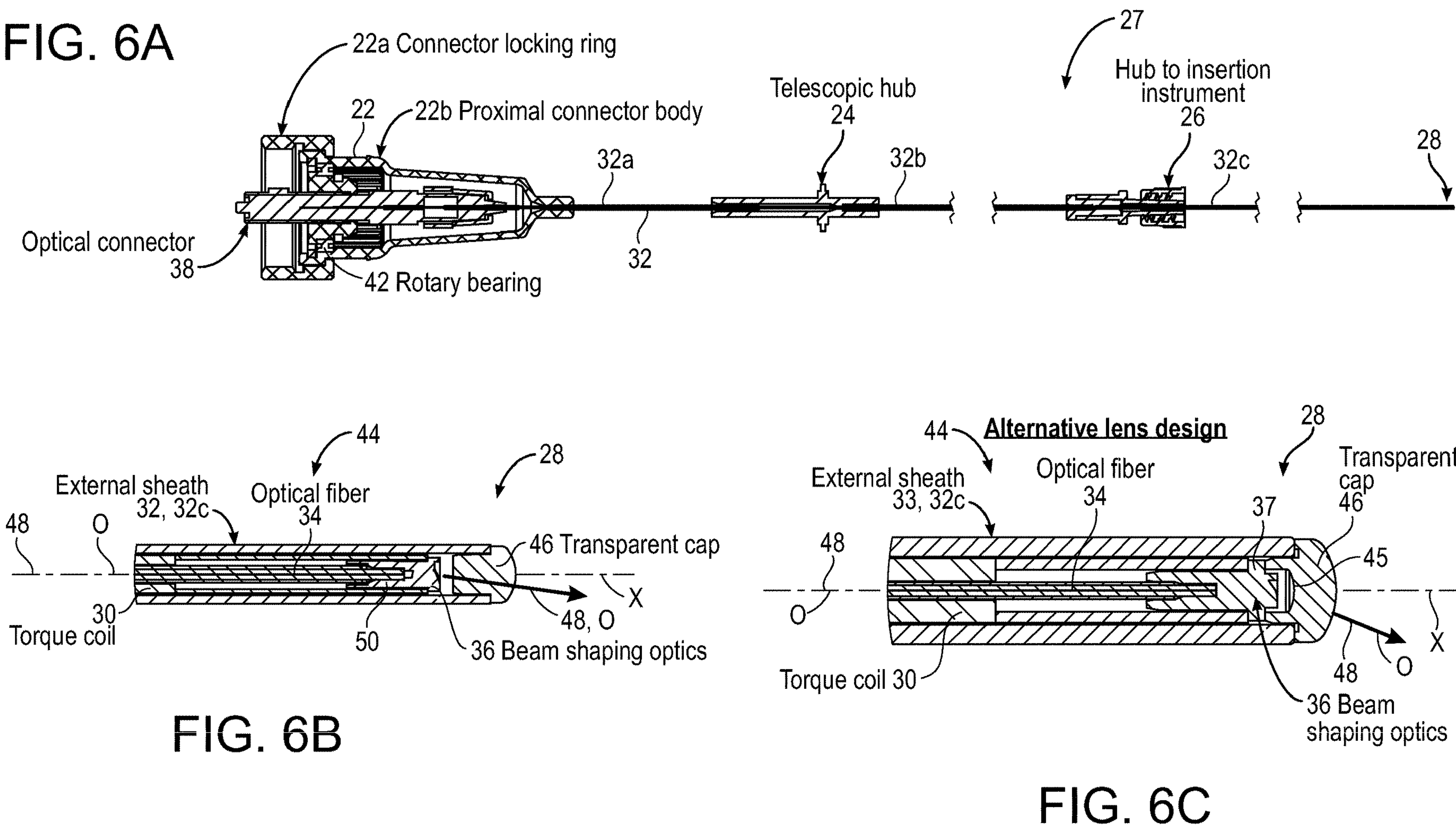
FIG. 6A is a side sectional drawing of a disposable forward imaging OCT probe.
FIGS. 6B and 6C are sectional views of embodiments of probe heads in the present disclosure.

FIG. 6A shows a side sectional view of the OCT probe 27 and embodiments of the probe head or tip regions 44 in FIGS. 6B and 6C. In FIG. 6B, the lens assembly 50 can include a forward facing lens exit window 72 having a forward facing annular mechanical stop, shoulder or ring 70 (FIGS. 8-10) encircling the exit lens profile or face 68 of exit lens 36 for limiting telescopic depth and preventing the lens face 68 from contacting the transparent cap 46 while rotating, thereby protecting the lens face 68 from damage. In FIG. 6C, the lens 36 can include a lateral radially extending mechanical stop, shoulder or diameter 37 for engaging the transparent cap 46, and the transparent cap 46 can have a recess 45 that provides a gap or clearance for the lens face 68 to prevent damage.

Figure 8:
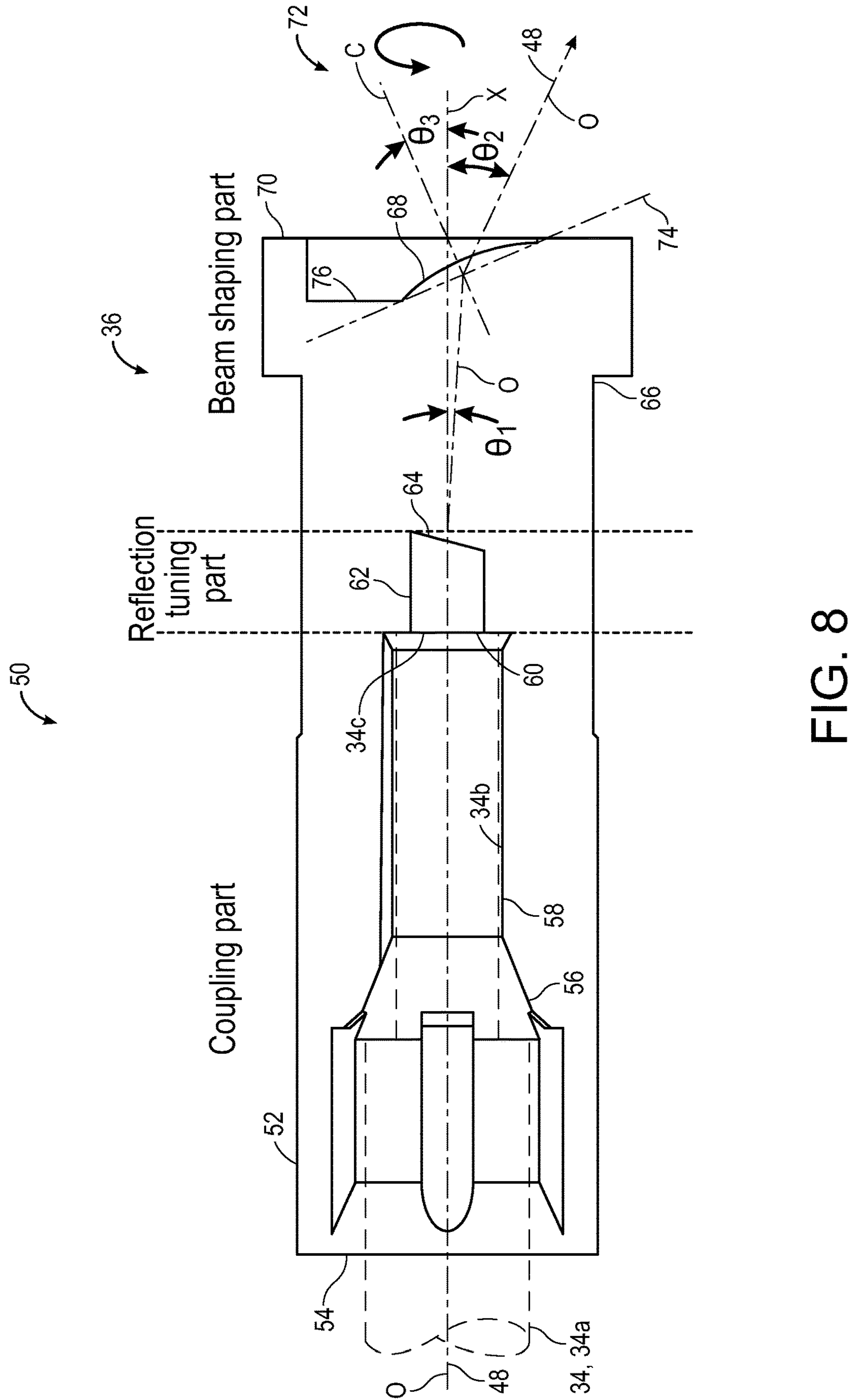
FIG. 8 is a side sectional view of an embodiment of a lens assembly in the present disclosure.
Figure 9:
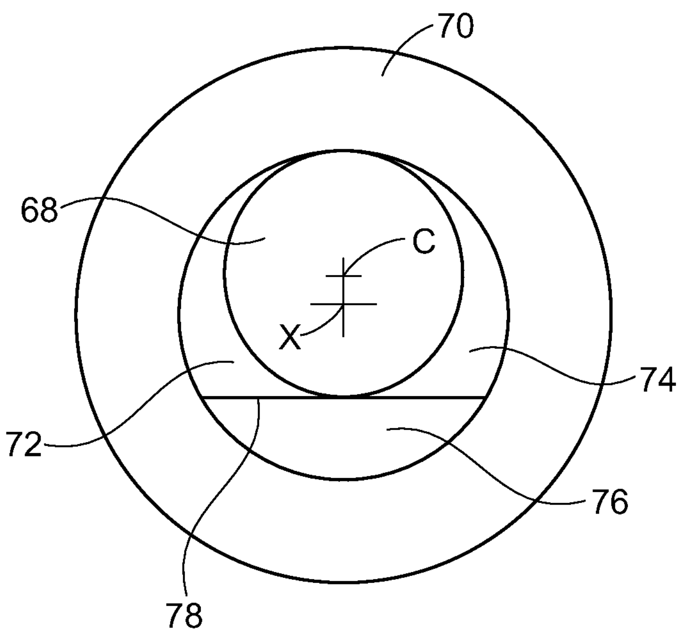
FIG. 9 is an end view of the lens assembly of FIG. 8.
Figure 10:
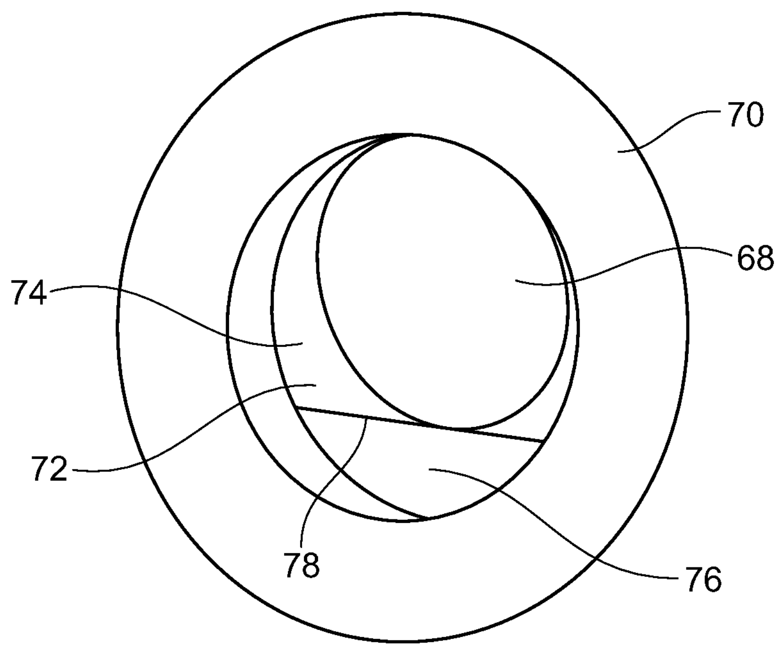
FIG. 10 is in an end perspective view of the lens assembly thereof.

Referring to FIGS. 8-10, lens 36 can be part of a lens assembly 50. The lens assembly 50 can include a retaining, coupling, connecting or securing sleeve, part or portion 52 for securing to the distal end of the fiber optic 34 along the optical axis O and the longitudinal central axis X. The fiber optic 34 can have an external jacket 34*a* and enters the entrance 54 of the connecting portion 52. The external jacket 34*a* can be stripped or removed at the distal end of the fiber optic 34 and enter an angled reducing diameter portion 56 before entering a smaller diameter securement or connecting recess or portion 58 where only the core and cladding of the fiber 34*b* is secured. The distal end 34*c* of the fiber 34*b* can terminate or abut against the distal end 60 of the connecting recess 58. The distal end of the fiber can be coated with a reflective coating to beam split and reflect some of the light 48 back through the fiber optic 34 as a control reference or common path reference light signal. In other embodiments, a separate reflective surface can be positioned at the distal end 34*c* of the fiber optic 34 at the distal end 60 of the connecting recess 58. The outer diameter of the coupling part 52 of the lens assembly 50 can be mounted or secured within the distal end of the inner cannula 30 which can abut against a distal shoulder 66, thereby providing rotation of the lens assembly 50. This can also protect the fiber optic 34 from torsion and stress during rotation. An air gap or pocket 62 can be positioned at the distal end 60 of the connecting recess 58 along the optical axis O and axis X, and can have a distal angled surface 64, which can be about 13°-15° relative to the plane of the distal end 60 of connecting recess 58. The angled surface 64 can prevent reflection of light back into the fiber optic 34 at the junction of the air gap 62 and lens 36 of the lens assembly 50. The air gap 62 with the angled surface 64 can direct, bend and focus light 48 received from the optical fiber 34 forwardly towards the exit lens face 68 of forward facing exit window 72 along the optical axis O at an outward angle $\theta_1$ relative to the central axis X. In some embodiments, the air gap 62 can be replace with a material with an angled surface 64 that has different optical properties than the material for lens 36 to bend and focus light 48. The exit lens 36 can receive the light 48 from air gap 62 and then further direct, bend and focus the light 48 with exit lens face 68 forwardly towards transparent cap 46 along optical axis O at an outward angle $\theta_2$ that is greater than $\theta_1$ relative to the central axis X. In some embodiments, $\theta_2$ can be about 10 to 20°, for example about 15°.

In some embodiments, the exit lens 36 of exit of window 72 can be a freeform lens having a convex exit lens surface, face or profile 68 defined by a high order polynomial. The exit lens face 68 can be encircled by the annular mechanical stop ring 70, and can extend from a periphery of exit window 72, terminating partway across the exit window 72. The convex exit surface of the exit lens face 68 can be tilted inwardly relative to the central axis X and can protrude from a tilted planar surface 74 that is recessed relative to annular mechanical stop ring 70. The center of the convex exit lens surface 68 along central axis C (FIG. 8) can be offset from the central axis X as seen in FIG. 9. The central axis C of the convex lens surface 68 can be at a 90° or right angle to the tilted planar surface 74 and can be at an angle $\theta_3$ relative to central axis X in the range of about 5 to 20°. The inner edge of the convex exit lens surface 68 can terminate at a recessed flat or planar surface portion 76 which can be parallel to the forward distal end surface of mechanical stop ring 70. The convex exit lens face 68 can occupy a portion of the area of the exit window 72, the remaining portions of the exit window 72 can be surfaces 74 and 76. The planar surfaces 74 and 76 can meet or intersect along a line 78. Surface 74 can be at an angle of about 5 to 20° relative to surface 76. The inner edge of the convex exit lens surface 68 can also terminate at line 78. The profile of exit lens face 68 can vary depending upon the dimensions of the lens assembly 50 and transparent cap 46. The outer diameter of lens assembly 50 can range from about 125 to 1200 μm. A high order polynomial defining the convex exit surface can be determined by inputting parameters of the probe head 44 into a computer program that calculates the polynomial that provides the desired shape of the exit lens face 68 to meet the parameters. The polynomial can be an order of 2 or greater, and can be in the range of 15 to 20.

While example embodiments have been particularly shown and described, it will be understood by those skilled in the art that various changes in form and details may be made therein without departing from the scope of the embodiments encompassed by the appended claims. Features of the different embodiments can be combined together and omitted.

What is claimed is:

1. An optical probe assembly comprising:

a lens assembly extending along a central axis for optically coupling to an optical fiber, the lens assembly comprising a forward facing exit window, the exit window having an exit lens with a convex exit surface, the exit lens extending from a periphery of the exit window and terminating partway across the exit window, such that the exit lens occupies less than a full width of the exit window and leaves an unlensed region across the exit window, the convex exit surface of the exit lens being tilted inwardly relative to the central axis, the exit lens for bending light received from the optical fiber forwardly out of the exit window at an outward angle relative to the central axis.

2. The optical probe assembly of claim 1 in which the exit lens bends and focuses the light out of the exit window at an outward angle relative to the central axis.

3. The optical probe assembly of claim 1, further comprising the optical fiber, the optical fiber being optically coupled to the lens assembly along the central axis for receiving light from a light source.

4. The optical probe assembly of claim 1, wherein the lens assembly further comprises a connecting portion that is integrally formed together with the exit window, the connecting portion configured to mechanically couple the lens assembly to the optical fiber.

5. The optical probe assembly of claim 4, wherein the connecting portion comprises a connecting recess extending along the central axis configured to receive a distal end of the optical fiber.

6. The optical probe assembly of claim 1, further comprising an inner cannula that houses the lens assembly and is rotationally disposed within an outer cannula.

7. The optical probe assembly of claim 6 in which the outer cannula has a distal end with a transparent cap secured thereto, though which light from the exit window passes.

8. The optical probe assembly of claim 7, further comprising a telescopic mechanism configured to translate the inner cannula and the lens assembly relative to the outer cannula.

9. The optical probe assembly of claim 8, wherein the lens assembly includes a mechanical stop configured to limit a telescoping depth of the inner cannula relative to the outer cannula.

10. The optical probe assembly of claim 3, further comprising a rotational element disposed at a proximal end of the optical fiber for rotating a distal end of the optical fiber and the lens assembly.

11. The optical probe assembly of claim 10, wherein the rotational element is rotationally coupled to a torque transfer element.

12. The optical probe assembly of claim 10, further comprising a connector assembly disposed at the proximal end of the optical fiber for connecting to the light source.

13. The optical probe assembly of claim 12, wherein the rotational element is a rotational motor or a rotary joint in operative arrangement with a rotational motor.

14. The optical probe assembly of claim 5, wherein the lens assembly includes a reflective surface at a distal end of the connecting recess of the connecting portion that is configured to generate a common path reference light signal.

15. The optical probe assembly of claim 14, wherein the lens assembly includes an angled surface spaced apart from the distal end of the connecting recess of the connecting portion along the central axis for bending light received from the optical fiber forwardly towards the exit lens at an outward angle relative to the central axis.

16. The optical probe assembly of claim 15, wherein the angled surface is at a distal end of an air gap.

17. The optical probe assembly of claim 1, wherein the exit lens is a freeform lens in which the convex exit surface is defined by a high order polynomial.

18. The optical probe assembly of claim 4, wherein the outer diameter of the lens assembly ranges from about 125 to 1200 um.

19. The optical probe assembly of claim 1, wherein the optical probe assembly is included in an optical coherence tomography system.

20. An optical probe assembly comprising:

a lens assembly extending along a central axis for optically coupling to an optical fiber, the lens assembly comprising a connecting portion that is integrally formed together with a forward facing exit window, the connecting portion including a connecting recess extending along the central axis for receiving a distal end of the optical fiber, the exit window having an exit lens, the lens assembly including an angled surface spaced apart from a distal end of the connecting recess of the connecting portion along the central axis for bending light received from the optical fiber forwardly towards the exit lens at an outward angle relative to the central axis, the exit lens for further bending light received from the angled surface forwardly out of the exit window at a further outward angle relative to the central axis.

21. The optical probe assembly of claim 20, wherein the angled surface is at a distal end of an air gap.

22. A method of operating an optical probe assembly, the optical probe assembly comprising:

a lens assembly extending along a central axis for optically coupling to an optical fiber, the lens assembly comprising a forward facing exit window, the exit window having an exit lens with a convex exit surface, the exit lens extending from a periphery of the exit window and terminating partway across the exit window, such that the exit lens occupies less than a full width of the exit window and leaves an unlensed region across the exit window, the convex exit surface of the exit lens being tilted inwardly relative to the central axis, the method comprising:

conveying light from the optical fiber to the exit lens and bending the light forwardly with the exit lens out of the exit window at an outward angle relative to the central axis; and rotating the exit lens about the central axis and directing the light forwardly in an expanding conical pattern for creating images forward of the probe assembly.

23. The method of claim 22 further comprising bending and focusing the light with the exit lens out of the exit window at an outward angle relative to the central axis.

24. The method of claim 22, further comprising delivering light from a light source to the optical fiber.

25. The method of claim 22, wherein the lens assembly further comprises a connecting portion that is integrally formed together with the exit window, the connecting portion configured to mechanically couple the lens assembly to the optical fiber.

26. The method of claim 25, wherein the connecting portion comprises a connecting recess extending along the central axis configured to receive a distal end of the optical fiber.

27. The method of claim 22, further comprising an inner cannula that houses the lens assembly and is rotationally disposed within an outer cannula.

28. The method of claim 27 in which the outer cannula has a distal end with a transparent cap secured thereto, though which light from the exit window passes.

29. The method of claim 28, further comprising translating the inner cannula and the lens assembly relative to the outer cannula with a telescopic mechanism.

30. The method of claim 29, further comprising limiting a telescoping depth of the inner cannula relative to the outer cannula with a mechanical stop included with the lens assembly.

31. The method of claim 29, further comprising rotating a distal end of the optical fiber and the lens assembly with a rotational element disposed at a proximal end of the optical fiber.

32. The method of claim 31, wherein the rotational element is rotationally coupled to a torque transfer element.

33. The method of claim 31, further comprising a connector assembly disposed at the proximal end of the optical fiber for connecting to the light source.

34. The method of claim 33, further comprising providing rotation with the rotational element, wherein the rotational element is a rotational motor or a rotary joint in operative arrangement with a rotational motor.

35. The method of claim 26, further comprising generating a common path reference light signal with a reflective surface at a distal end of the connecting recess of the connecting portion of the lens assembly.

36. The method of claim 35, further comprising bending light received from the optical fiber forwardly towards the exit lens at an outward angle relative to the central axis with an angled surface spaced apart from the distal end of the connecting recess of the connecting portion of the lens assembly along the central axis.

37. The method of claim 36, wherein the angled surface is at a distal end of an air gap.

38. The method of claim 22, wherein the exit lens is a freeform lens in which the convex exit surface is defined by a high order polynomial.

39. The method of claim 25, wherein the outer diameter of the lens assembly ranges from about 125 to 1200 um.

40. The method of claim 22, wherein the optical probe assembly is included in an optical coherence tomography system.

41. A method of operating an optical probe assembly, the optical probe assembly comprising:

a lens assembly extending along a central axis for optically coupling to an optical fiber, the lens assembly comprising a connecting portion that is integrally formed together with a forward facing exit window, the connecting portion including a connecting recess extending along the central axis for receiving a distal end of the optical fiber, the exit window having an exit lens, the lens assembly including an angled surface spaced apart from a distal end of the connecting recess of the connecting portion along the central axis, the method comprising:

with the angled surface, bending light received from the optical fiber forwardly towards the exit lens at an outward angle relative to the central axis, and the exit lens further bending light received from the angled surface forwardly out of the exit window at a further outward angle relative to the central axis; and rotating the exit lens about the central axis and directing the light forwardly in an expanding conical pattern for creating images forward of the probe assembly.

42. The method of claim 41, wherein the angled surface is at a distal end of an air gap.

* * * * *